US00PP31656P2

(12) United States Plant Patent
van Geest

(10) Patent No.: US PP31,656 P2
(45) Date of Patent: Apr. 14, 2020

(54) ***FICUS* PLANT NAMED 'ESFIBU1802'**

(50) Latin Name: *Ficus bussei*
Varietal Denomination: ESFIBU1802

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 16/501,282

(22) Filed: Mar. 16, 2019

(51) Int. Cl.
*A01H 5/00* (2018.01)

(52) U.S. Cl.
USPC ..... Plt./211

(58) Field of Classification Search
USPC ..... Plt./211
CPC ..... A01H 5/00
See application file for complete search history.

*Primary Examiner* — Annette H Para
(74) *Attorney, Agent, or Firm* — Samuel R. McCoy, Jr.

(57) ABSTRACT

A new and distinct variety of *Ficus* plant named 'ESFIBU1802' which is characterized by the combination of relatively large foliage on a compact plant, ribbed to bullate foliage with conspicuous venation, foliage which is held nearly vertical to slightly pendulous, and the stability of all characteristics from generation to generation.

3 Drawing Sheets

Latin name of the genus and species: The Latin name of the genus and species of the novel variety disclosed herein is *Ficus bussei*.

Variety denomination: The inventive variety of *Ficus* disclosed herein has been given the variety denomination 'ESFIBU1802'.

BACKGROUND OF THE INVENTION

Parentage: 'ESFIBU1802' originated as a naturally occurring, whole-plant mutation of an unnamed *Ficus bussei* plant (not patented). In the summer of 2015, the inventor discovered the mutation at his commercial greenhouse in Gravenzande, The Netherlands, growing amongst a cultivated population of *Ficus bussei* plants. The mutation was noted for its relatively large, ribbed foliage on a compact plant and was subsequently isolated for further evaluation in order to confirm the distinctness and stability of the characteristics first observed. Upon confirmation of distinctness and stability, 'ESFIBU1802' was selected for commercialization.

Asexual Reproduction: Asexual reproduction of 'ESFIBU1802', by way of stem cuttings, was first initiated in the summer of 2015 at a commercial greenhouse in Gravenzande, The Netherlands. Through five subsequent generations, the unique features of this cultivar have proven to be stable and true to type.

SUMMARY OF THE INVENTION

The cultivar 'ESFIBU1802' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'ESFIBU1802'. These characteristics in combination distinguish 'ESFIBU1802' as a new and distinct *Ficus* cultivar:

1. *Ficus* 'ESFIBU1802' exhibits relatively large foliage on a compact plant; and
2. *Ficus* 'ESFIBU1802' exhibits ribbed to bullate foliage with conspicuous venation; and
3. *Ficus* 'ESFIBU1802' exhibits green foliage with light green venation; and
4. *Ficus* 'ESFIBU1802' exhibits foliage which is held nearly vertical to slightly pendulous.

BOTANICAL DESCRIPTION OF THE PLANT

Figure 1:
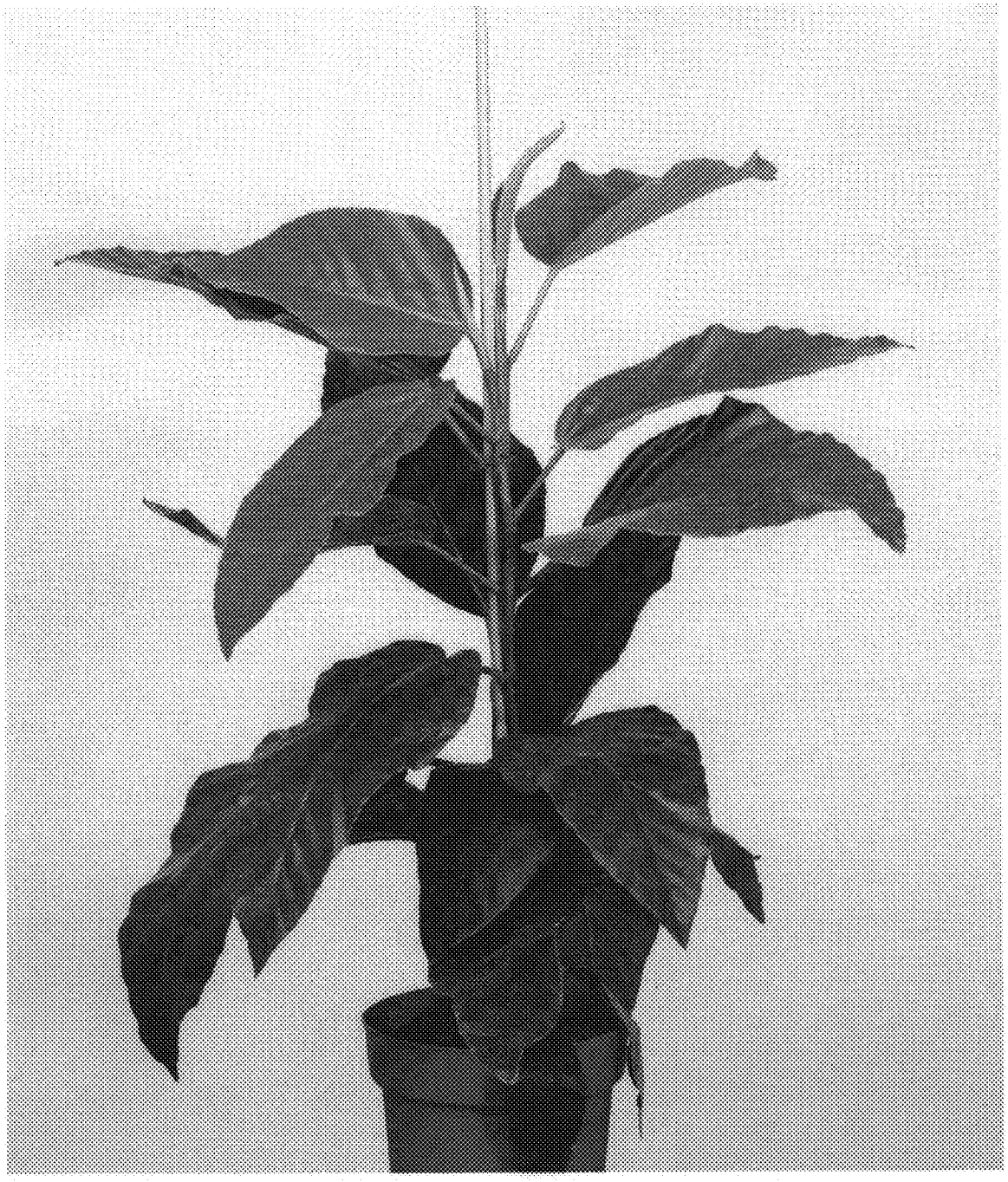
FIG. 1 illustrates, as nearly true as it is reasonably possible to make the same in color photographs of this type, an exemplary plant of 'ESFIBU1802' grown in a commercial greenhouse in Gravenzande, The Netherlands. This plant is approximately 20 weeks old, shown planted in a 15 cm container.
Figure 2:
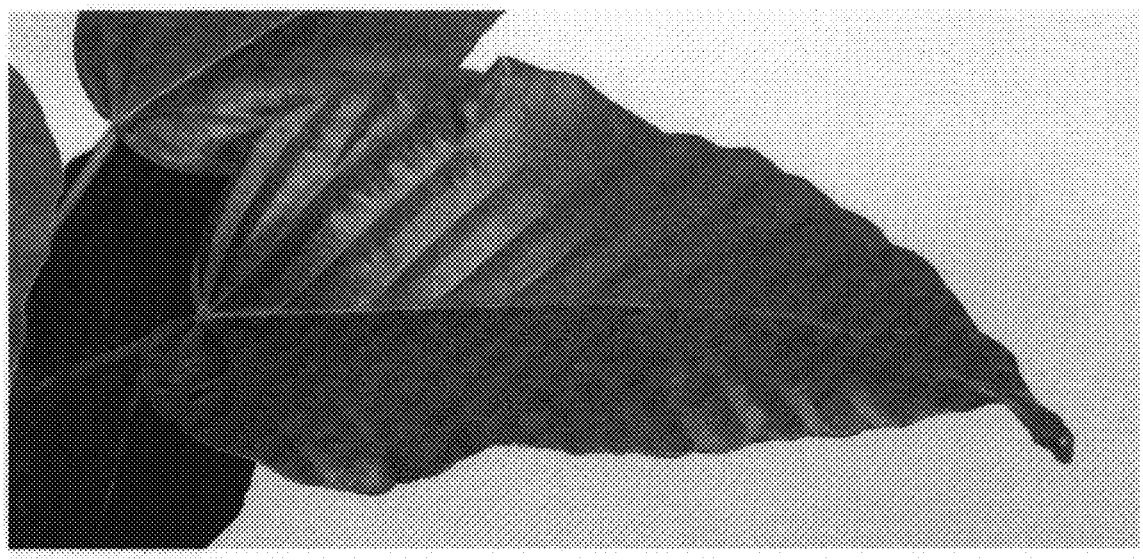
FIG. 2 illustrates, as nearly true as it is reasonably possible to make the same in color photographs of this type, the adaxial surface of the mature foliage of 'ESFIBU1802'.
Figure 3:
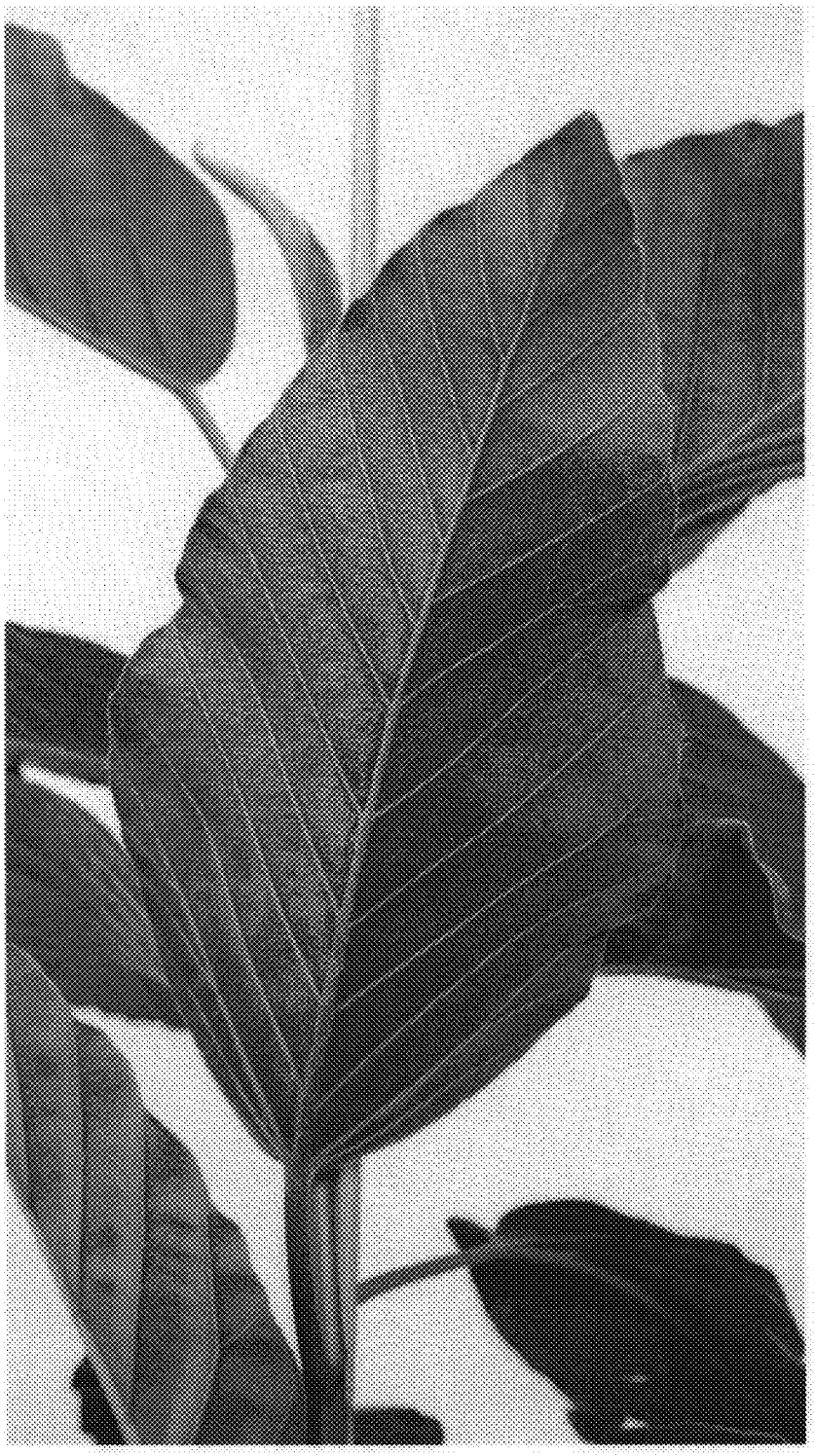
FIG. 3 illustrates, as nearly true as it is reasonably possible to make the same in color photographs of this type, the abaxial surface of the mature foliage of 'ESFIBU1802'.

The following observations and measurements were made in February of 2019 and describe a sample set of six 20 week-old 'ESFIBU1802' plants grown in 15 cm nursery pots at a greenhouse in Gravenzande, The Netherlands. Plants were produced in a greenhouse with full sun exposure, ebb and flood irrigation tables, no supplemental fertilizer, and no preventative or pest control measures utilized.

Those skilled in the art will appreciate that certain characteristics will vary with older or, conversely, with younger plants. 'ESFIBU1802' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'ESFIBU1802' and comparisons with the parent plant and most similar commercial variety of *Ficus* are provided below.

Plant description:

*Growth habit.*—Upright.

*Plant form.*—Broad oblong to obovate.

*Average height.*—70.7 cm from the soil level to the top of the foliar plane.

*Plant spread.*—Average of 70.5 cm.

*Growth rate.*—Moderately fast to fast.

*Plant vigor.*—Moderately vigorous to vigorous.

*Propagation type.*—Stem cuttings.

*Time to produce a rooted cutting.*—Approximately 40 days to produce a rooted cutting at approximately 25 degrees Celsius.

*Time to produce a finished plant.*—Approximately 18 weeks to produce a marketable finished plant in a 17 cm pot.

*Disease resistance.*—Neither resistance nor susceptibility to typical *Ficus bussei* pests and diseases has been observed.

*Environmental tolerances.*—Adapt to, at least, USDA Zones 10 through 13 and temperatures as high as 40 degrees Celsius; moderate to high tolerance to rain; low to moderate tolerance to wind.

Root system:

*General.*—Moderately dense, moderately branched rooting; roots are slightly fibrous.

*Distribution in the soil profile.*—Shallow to moderately deep.

*Diameter of roots.*—0.75 mm on average.

*Texture.*—Smooth; no root hairs.

*Color.*—Greyed-yellow, nearest to RHS 161D.

Stem:

*General branching habit.*—Basally branching main stems; no lateral branching. Pinching isn't required but will improve branching. Stems produce a milky exudate when damaged.

*Quantity of stems.*—3.

*Length.*—Approximately 52.0 cm.

*Diameter.*—Approximately 0.9 cm.

*Internode length.*—Approximately 7.5 cm.

*Attitude.*—Slightly upward to near vertical.

*Aspect.*—Rounded; slightly angular.

*Texture.*—Sparsely covered with lenticels; lenticels are approximately 1.5 mm long and 0.75 mm wide and are colored greyed-brown, nearest to RHS 199D. Stems are moderately to densely covered with very short strigose hairs with an average length of 0.2 mm. Hairs are colored greyed-brown, nearest to RHS 199C.

*Luster.*—Slightly glossy.

*Strength.*—Strong.

*Color, juvenile.*—Nearest to in between green, RHS 143B, and yellow-green, RHS 144A.

*Color, mature.*—Yellow-green, nearest to a combination of RHS 146B and 146C.

*Color at internodes.*—Yellow-green, nearest to RHS 148A.

*Color of the oldest wood.*—Yellow-green, nearest to RHS 148A, and axially striped greyed-brown, nearest to RHS 199B.

Foliage:

*Arrangement.*—Alternate.

*Division.*—Simple.

*Quantity.*—7 leaves per lateral branch.

*Attitude.*—At an average angle of 60 degrees to the stem.

*Lamina.*—Shape — Ovate. Aspect — Slightly carinate. Dimensions — 33.2 cm long and 18.0 cm wide. Apex — Acute. Base — Cordate to truncate. Margin — Entire, very slightly angulate; moderately undulate. Texture of adaxial surface — Ribbed to bullate, glabrous and glossy, with small orbicular glands visible along the margins; glands are approximately 0.2 mm in diameter and are colored yellow-green, nearest to RHS 150C. Texture of abaxial surface — Ribbed to bullate, and moderately covered with a thin woolly pubescence which is colored green-white, nearest to RHS 157D. Color — Juvenile foliage, adaxial surface — Green, nearest to RHS 137A, and veined yellow-green, nearest to RHS N144A. Juvenile foliage, abaxial surface — Yellow-green, nearest to RHS 147B, and veined lighter, nearest to RHS 146D. Mature foliage, adaxial surface — Green, nearest to in between RHS NN137A and 139A. Mature foliage, abaxial surface — Greyed-green, nearest to RHS 191A. Venation — Pattern — Main and secondary veins are pinnate; tertiary veins are reticulate. Color, adaxial surface — Yellow-green, nearest to a mixture of RHS 145A and 145B. Color, abaxial surface — Yellow-green, nearest to RHS 145C.

*Stipule.*—Not present.

*Petiole.*—Length — 8.2 cm. Diameter — 0.7 cm. Strength — Strong. Texture — Moderately covered with a thin wooly pubescence which is colored greyed-brown, nearest to RHS 199C. Luster — Slightly glossy. Color, adaxial surface — Yellow-green, nearest to RHS 146C. Color, abaxial surface — Yellow-green, nearest to RHS 144B.

Inflorescence: No flowering has been observed to date.

Comparison with the parent plant: Plants of the new cultivar 'ESFIBU1802' differ from the parent, an unnamed *Ficus bussei* plant (not patented), in the following characteristics described in Table 1 below.

TABLE 1

| Characteristic | 'ESFIBU1802' | The parent. |
|---|---|---|
| Growth habit. | More compact than the parent. | Less compact compared to 'ESFIBU1802'. |
| Internode length. | Shorter than the parent. | Longer than 'ESFIBU1802'. |
| Foliage size. | Smaller than the parent. | Larger than 'ESFIBU1802'. |
| General coloration of the mature foliage. | Darker green. | Lighter green. |

Comparison with the closest known comparator: Plants of the new cultivar 'ESFIBU1802' differs from the variety, *Ficus* sp. 'ESPE1803', for which a United States plant patent application is being filed concurrently with the instant application, in the following characteristics described in Table 2 below.

TABLE 2

| Characteristic | 'ESFIBU1802' | 'ESPE1803' |
|---|---|---|
| Foliage shape. | Ovate. | Cordate. |
| General coloration of the foliage. | Lighter green. | Darker green. |
| General coloration of the foliage venation. | Green. | White. |
| General coloration of the stems and branches. | Green. | Yellow-green. |

That which is claimed is:

1. A new and distinct variety of *Ficus* plant named 'ESFIBU1802', substantially as described and illustrated herein.

* * * * *